United States Patent [19]

Simons

[11] Patent Number: 5,381,896

[45] Date of Patent: Jan. 17, 1995

[54] PRESENTATION TRAY FOR SURGICAL INSTRUMENTS

[75] Inventor: Teresa M. Simons, Piscataway, N.J.

[73] Assignee: Ethicon, Inc., Somerville, N.J.

[21] Appl. No.: 133,414

[22] Filed: Oct. 6, 1993

[51] Int. Cl.⁶ .......................................... B65D 85/20
[52] U.S. Cl. .................................. 206/370; 206/564
[58] Field of Search ............... 206/363, 364, 366, 369, 206/370, 372, 438, 471, 564, 570

[56] References Cited

U.S. PATENT DOCUMENTS

| | | | |
|---|---|---|---|
| 240,595 | 4/1881 | Laraway et al. | 206/372 |
| 3,116,828 | 1/1964 | Glassman | 206/564 |
| 3,285,409 | 11/1966 | Loran | 206/564 |
| 4,111,302 | 9/1978 | Roth | 206/363 |
| 4,577,755 | 3/1986 | Ramsay | 206/370 |
| 4,643,303 | 2/1987 | Arp et al. | 206/370 |
| 5,048,684 | 9/1991 | Scott | 206/471 |
| 5,156,267 | 10/1992 | Yates, Jr. et al. | 206/364 |
| 5,193,679 | 3/1993 | White | 206/363 |
| 5,199,567 | 4/1993 | Discko, Jr. | 206/369 |

*Primary Examiner*—Jimmy G. Foster
*Attorney, Agent, or Firm*—Paul A. Coletti

[57] ABSTRACT

A tray is described herein for holding and displaying a number of surgical instruments. Each of these instruments have a handle and contain an elongated shaft extending from the handle. The shaft itself defines a longitudinal axis. The tray contains a base defining a first plane for supporting the shafts of the instruments. There is further described a handle holding portion extending from the base. The handle holding portion contains a first side wall attached to the base and a bottom for holding the handle extending from the first side wall. The bottom defines a second plane. The first and second planes are not parallel. A package which holds the tray of this invention has a first surface which supports the base and a second surface which supports the bottom of the handle portion. Ideally, there is also a third surface extending from the base. The first and third surfaces are co-planar and capable of supporting the package and the tray containing the instruments. The tray is removed from the package and with the surgical instruments contained thereon. In this fashion, the tray is supported on a stand by the bottom and the surface extending from the second side wall.

2 Claims, 3 Drawing Sheets

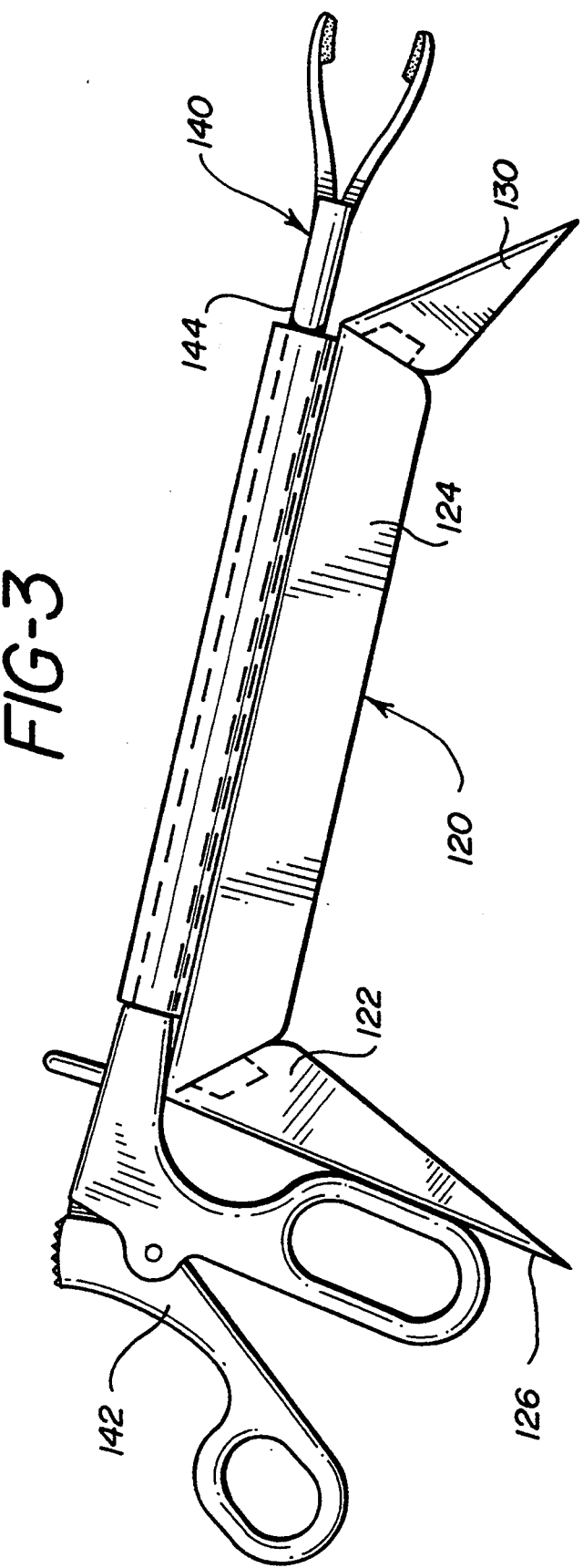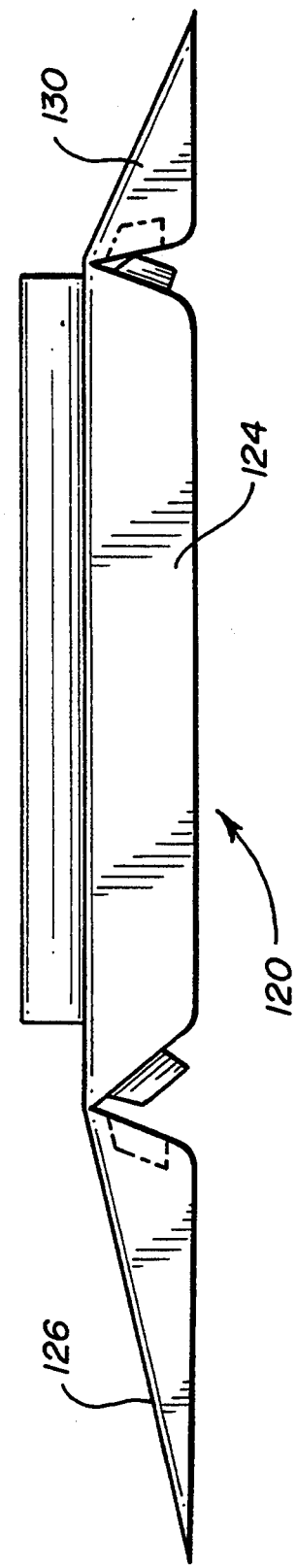

PRESENTATION TRAY FOR SURGICAL INSTRUMENTS

FIELD OF THE INVENTION

Generally, this invention relates to trays for surgical instruments. More specifically this invention relates to presentation trays for a group of surgical instruments, particularly those instruments useful in laparoscopic surgery.

BACKGROUND OF THE INVENTION

Generally, instruments used in laparoscopic surgery are removed from individual sterile packages and placed on a surgical stand (Mayo Stand), or the surgical instruments are contained in a kit which may contain more than one surgical instrument. However, when arranged on the stand, either the entire kit is placed flat on the stand, or the instruments are removed individually from the kit and placed on the stand as if they had been taken from a sterile package.

Thus, in either event, there is no useful mechanism for containing the surgical instruments in a compact, easy-to-view manner. In this fashion, therefore, there has not been provided a simple easy-to-use presentation instrument which allows the surgical instruments to be taken out of the kit and placed on the stand without individual removal and subsequent placement.

Also, since only two or three ports are usually available at any one time, the instruments are often removed from the body cavity and replaced on the stand, only to be needed and used again. This design helps facilitate the containment, ordering and identification of instruments used at multiple distinct intervals throughout a single procedure. And, due to the high degree of similarity of these instruments with exception to the working end, this tray helps delineate each instrument from the others by making the working end more visible and improves the use of color code identification by ordering the instruments.

It is, therefore, an object of this invention to provide a compact viewing tray capable of being emplaced in a sterile package containing a group of surgical instruments. It is also an object of the current invention to provide these instruments after removal from the tray in a much more visible manner. Finally, it is an object of this invention to provide a receptacle for the instruments so that they can be taken and removed from the stand and adequately counted during and after surgery without the need to arrange the instruments on the stand individually, and thereby take unnecessary time to, effect such arrangement.

SUMMARY OF THE INVENTION

These and other objects of the invention are described in a tray for holding and displaying a number of surgical instruments. Each of these instruments have a handle and contain an elongated shaft extending from the handle. The shaft itself defines a longitudinal axis. The tray contains a base defining a first plane for supporting the shafts of the instruments. There is further described a handle holding portion extending from the base. The handle holding portion contains a first side wall attached to the base and a bottom for holding the handle extending from the first side wall. The bottom defines a second plane. The first and second planes are purposely configured so that they are not parallel. A third side is also critical to establish stability of the erected tray and to preclude the working ends of the instruments from becoming damaged by suspending them above the Mayo Stand.

Furthermore, there is contained in the invention an outer package which holds the tray of this invention. This package has a first surface which supports the base and a second surface which supports the bottom of the handle portion. Ideally, there is also a third surface extending from the base. The first and third surfaces are co-planar and capable of supporting the package and the tray containing the instruments. The outer package may take other forms including a paperboard or foam design.

In use, the tray is removed from the package and with the surgical instruments contained thereon. The tray contains a second side wall extending from the base which ends in a surface which is co-planar with the bottom. In this fashion, the tray is supported on a stand by the bottom and the surface extending from the second side wall. The instruments abut the first side walls along their handles and the base along their shafts. The instruments are therefore arranged in a very orderly fashion with their handles facing upward to be removed by the user and replaced on the tray. The tray is designed such that upon erection of the tray, the layered instruments rotate under their own weight and as such are self-orienting. Thus, user interface, and the need to continuously provide inventory are both eased by this invention.

DESCRIPTION OF THE DRAWINGS

This invention will be better understood in conjunction with the attached drawings wherein;

FIG. 3 is a side view of an alternate embodiment; and

FIG. 4 is a side view of the embodiment in the collapsed position.

DETAILED DESCRIPTION OF THE INVENTION

Figure 1:
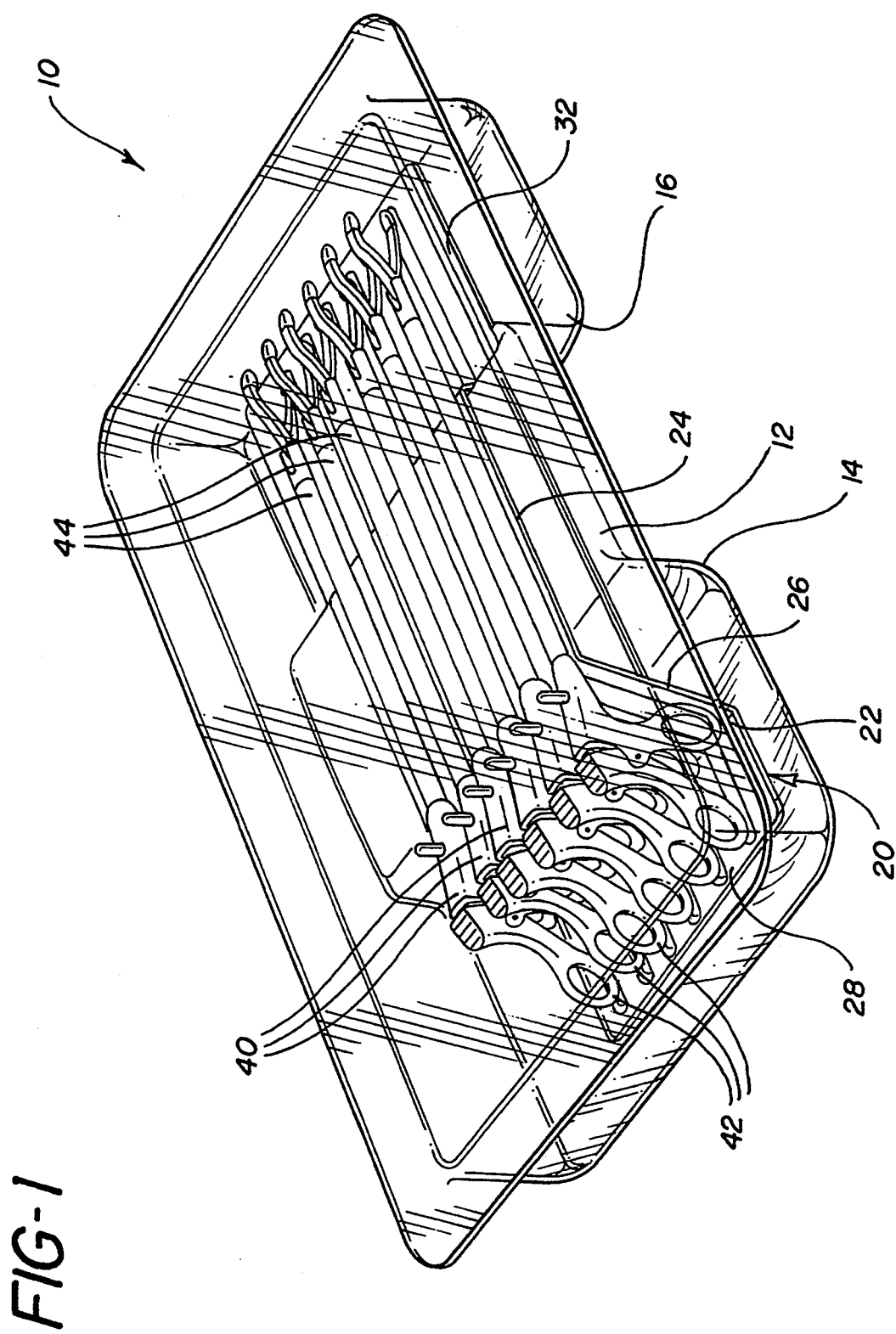
FIG. 1 is a perspective view of the package and tray of this invention.
Figure 2:
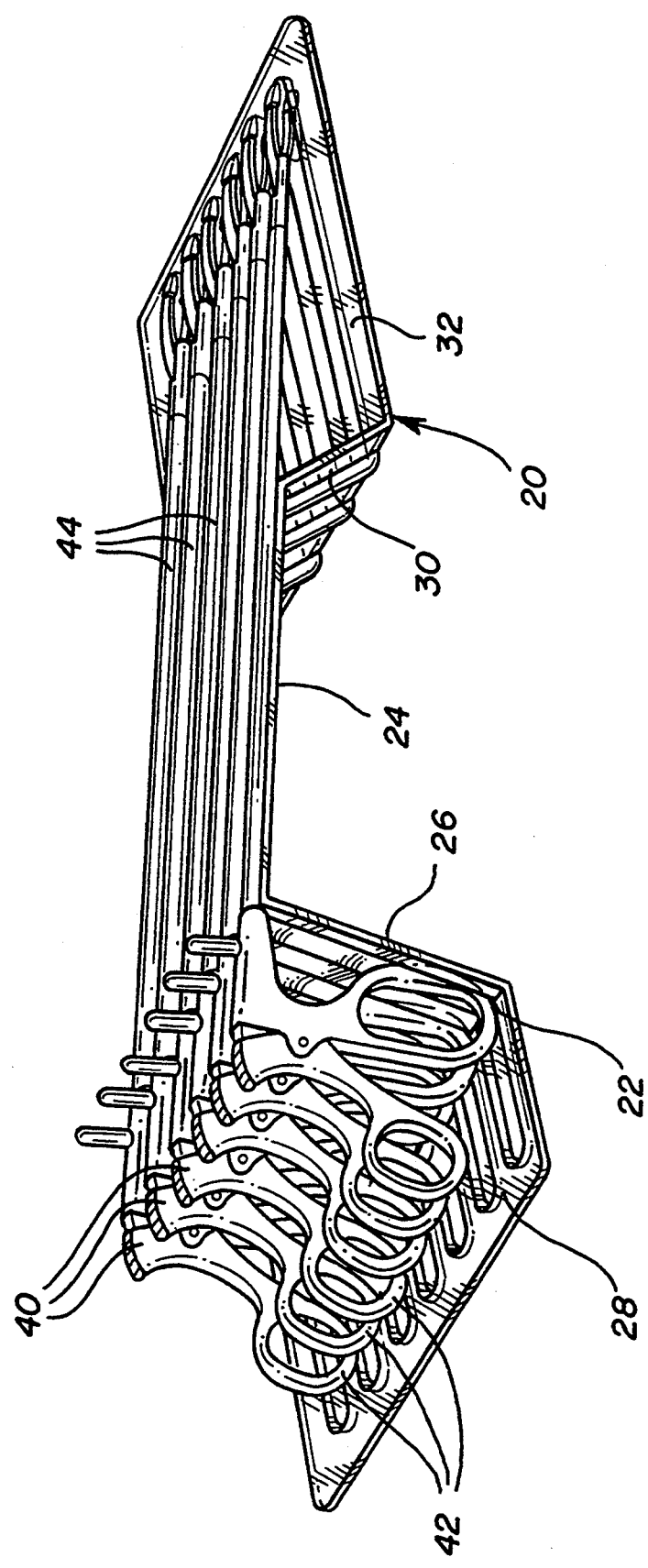
FIG. 2 is a perspective view of the tray of this invention after removal from the package and placed on a surgical stand.

The tray 20 and package 10 of this invention are generally seen in FIG. 1. There, a series of surgical instruments 40 are placed in the package 10 and arranged so that their handles 42 fit into a handle holding portion 22. The shafts 44 extend from the handles 42 and are placed in a planar fashion across the base portion 24 of the tray 20. The base portion 24 of the tray 20 is generally planar, and extends at least the length of a portion of the shafts 44 of the instruments 40. As better seen in FIG. 2, extending from the base 24 there is a first side wall 26 which ends in a bottom 28. The bottom 28 and first side wall 26 are adequately capable of adequately holding the handle portions 42 of the surgical instruments 40.

Also extending from the base 24 at the distal ends of the shafts 44 of the instruments 40 is a second side wall 30. The second side wall 30 terminates in a surface 32 which when placed on the surgical stand is co-planar with the bottom 28 of the tray 20.

The tray 20 of this invention is contained in a package 10 as better seen in FIG. 1. This package 10 contains a first surface 12 which has a surface area at least the area of the base 24. There is also a second surface 14 which supports the bottom 28 of the tray 20. This second surface 14 has a surface area at least that of the bottom 28 of the tray 20.

Also, this package 10 contains a third surface 16 which extends from the side opposite of the first surface 12. The third surface 16 is generally parallel and co-planar with the second surface 14. This allows the tray 20 with instruments 40 stacked thereon to be adequately placed on a surgical stand in package 10, before use of the tray 20. Also, it will be seen that the first and second and third surfaces 12, 14, 16 are contained in parallel planes. In this fashion, the instruments can be stacked on the tray 20 and into a package 10. Kits are arranged so that surgical instruments are generally placed with shafts 44 parallel to the plane of the first and third surfaces 12, 16. Thus, this compact storage allows for easy shipping. When it is desired to use the instruments on the surgical stand, the seal of the package 10 is removed so that the tray 20 is now exposed. The tray 20 is removed from the bottom of the package 10. The tray 20 itself is placed on the surgical stand so that the bottom 28 and the surface 32 of the second side wall 30 are now co-planar. In this fashion, the shafts 44 of the instruments 40 are placed along the plane of the base 24. Thus, the plane of the bottom 28 which is not parallel to the plane of the base 24 causes the shafts 44 to be tilted with respect to the plane of the bottom 28 of tray 20. This causes the shafts 44 and handles 42 to extend in a ready-to-grip fashion. In this way, the instruments 40 can be removed at the handles 42 very readily from the tray 20 of this invention.

After their use, when it is desired to return the instruments back onto the tray 20 of this invention, the user merely replaces the handle 42 into the portion of the tray formed by the intersection of the bottom 28 and the first side wall 26. The shafts 44 come to rest against the plane of the base 24. In this light, it is also very easy to perform an inventory check.

An alternate tray 120 of this invention are generally seen in FIGS. 3 and 4. There, a series of surgical instruments 140 are placed in the package 10 and arranged so that their handles 142 fit into a handle holding portion 122. The shafts 144 extend from the handles 142 and are placed in a planar fashion across the base portion 124 of the tray 120. The base portion 124 of the tray 120 is generally planar, and extends at least the length of a portion of the shafts 144 of the instruments 140. Extending from the base 124 there is a first side wall 126. The first side wall 126 is adequately capable of adequately holding the handle portions 142 of the surgical instruments 140.

Also extending from the base 124 at the distal ends of the shafts 144 of the instruments 140 is a second side wall 130. The second side wall 130 when erected and placed on the surgical stand supports as the first side wall 126.

The tray 120 of this invention is contained in an outer package 10 as better seen in FIG. 1. This package 10 contains a first surface 12 which has a surface area at least the area of the base 24. There is also a second surface 14 which supports the collapsed sidewall 126 of the tray 120. This second surface 14 has a surface area at least that of the side wall 126 of the tray 120.

Also, this package 10 contains a third surface 16 which extends from the side opposite of the first surface 12. The third surface 16 is generally parallel and co-planar with the second surface 14. This allows the tray 20 with instruments 40 stacked thereon to be adequately placed on a surgical stand in package 10, before use of the tray 20. Also, it will be seen that the first and second and third surfaces 12, 14, 16 are contained in parallel planes. In this fashion, the instruments can be stacked on the tray 20 and into a package 10. Kits are arranged so that surgical instruments are generally placed with shafts 144 parallel to the plane of the first and third surfaces 12, 16. Thus, this compact storage allows for easy shipping. When it is desired to use the instruments on the surgical stand, the seal of the package 10 is removed so that the tray 20 is now exposed. The tray 20 is removed from the bottom of the package 10. The tray 20 itself is placed on the surgical stand so that the side walls 126, 130 and are at opposite angles relative to the base 124. In this fashion, the shafts 144 of the instruments 140 are placed along the plane of the base 124. The width of the side wall 126 is greater than the width of the sidewall 130. Thus, the plane of the base 124 is inclined upon erection and placement on the surgical stand. This causes the shafts 144 and handles 142 to extend in a ready-to-grip fashion. In this way, the instruments 140 can be removed at the handles 142 very readily from the tray 120 of this invention.

After their use, when it is desired to return the instruments back onto the tray 120 of this invention, the user merely replaces the handle 142 into the portion of the tray formed by the intersection of the side wall 126 and the base 124. The shafts 144 come to rest against the plane of the base 124. In this light, it is also very easy to perform an inventory check.

The invention described herein is now to be understood by the attached claims and their equivalents.

We claim:

1. A tray for holding and displaying a plurality of surgical instruments, said instruments having a handle and an elongated shaft extending from said handle, comprising:

a base defining a first plane for supporting the shafts of said instruments;

a handle holding portion extending from said base, said handle holding portion having a first side wall, and a bottom for holding said handle extending from said side wall, said bottom defining a second plane;

wherein said first and second planes are not parallel; and further containing a second side wall extending from said base, and said second side wall terminating at a surface co-planar with said bottom, said tray contained in a package having a bottom, said package bottom having a first surface having a surface area at least that of said base and a second surface spaced apart from said first surface and having a surface area at least that of said handle holding portion bottom.

2. The tray of claim 1 wherein said package contains a third surface spaced apart from said base, and said first and third surfaces co-planar and capable of supporting said package and said tray containing said instruments.

* * * * *